(12) United States Patent
Opitz et al.

(10) Patent No.: US 6,617,165 B1
(45) Date of Patent: Sep. 9, 2003

(54) METHOD FOR AUTOMATICALLY TESTING AND CONTROLLING SURFACE-ACTIVE CONTENTS IN AQUEOUS SOLUTIONS USED IN A PROCESS

(75) Inventors: Werner Opitz, Langenfeld (DE); Hans-Willi Kling, Wuppertal (DE); Ibolya Bartik-Himmler, Odenthal (DE); Ludger Buetfering, Cologne (DE); Friedhelm Siepmann, Essen (DE); Bernd Schenzle, Troy, MI (US); Wolfgang Krey, Wuppertal (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 09/647,068

(22) PCT Filed: Mar. 23, 1999

(86) PCT No.: PCT/EP99/01939

§ 371 (c)(1),
(2), (4) Date: Nov. 27, 2000

(87) PCT Pub. No.: WO99/51981

PCT Pub. Date: Oct. 14, 1999

(30) Foreign Application Priority Data

Apr. 1, 1998 (DE) ......................................... 198 14 500

(51) Int. Cl.[7] ............................................... G01N 35/08
(52) U.S. Cl. ........................ 436/55; 436/163; 436/103; 436/104
(58) Field of Search .................... 422/3, 7, 15; 436/55, 436/103, 104, 181

(56) References Cited

U.S. PATENT DOCUMENTS

| 3,900,373 | A | * | 8/1975 | Ralston, Jr. .................. 204/99 |
| 4,213,796 | A | * | 7/1980 | Shaffer ........................ 134/26 |
| 4,268,397 | A | * | 5/1981 | Horie et al. |
| 4,374,681 | A | * | 2/1983 | Schueneman ............... 148/241 |
| 4,713,772 | A | * | 12/1987 | Carlson ....................... 364/496 |
| 4,887,453 | A | * | 12/1989 | Carter et al. ................. 204/401 |
| 5,396,416 | A | * | 3/1995 | Berkowitz et al. ............. 700/45 |
| 5,503,682 | A | * | 4/1996 | Mueller-Kirschbaum et al. .......... 134/2 |
| 5,710,048 | A | * | 1/1998 | Ernst et al. .................. 436/119 |
| 5,721,143 | A | * | 2/1998 | Smith et al. ................. 436/163 |
| 5,824,270 | A | * | 10/1998 | Rao ........................ 422/82.09 |
| 2001/0000334 | A1 | * | 4/2001 | Ruth et al. .................. 436/181 |

FOREIGN PATENT DOCUMENTS

| DE | 195 38 932 | 4/1997 | |
| EP | 0 750 189 | 12/1996 | |
| JP | 09033514 A | * 2/1997 | .......... G01N/33/18 |
| WO | WO95/18368 | 7/1995 | |

OTHER PUBLICATIONS

Agudo et al. "Continuous liquid–liquid extraction with on–line monitoring for the determination of anionic surfactants in wafers", Analyst, Sep. 1994, v. 199, p. 2097–2100.*
Analyst 114, p. 1435.

* cited by examiner

Primary Examiner—Jill Warden
Assistant Examiner—Yelena Gakh
(74) Attorney, Agent, or Firm—Stephen D. Harper

(57) ABSTRACT

A method for the automatic monitoring and control of the content of surfactants of an aqueous process solution, wherein, under program control: a sample having a predetermined volume is taken from the aqueous process solution; the content of surfactants in the sample is determined utilizing measuring equipment capable of analyzing the sample; the results of the analysis are output by the system; the functional capacity of the measuring equipment is checked by determining the surfactant content of one or more standard solutions if the results of the analysis of the content of surfactants on two consecutive drawn samples differs by a preselected value; and corrective action is automatically taken if the check of the measuring equipment reveals any problems. Bath maintenance measures may be initiated automatically or by request from a remote location according to pre-determined criteria. The method reduces the number of staff for bath monitoring and bath maintenance and increases process safety.

24 Claims, No Drawings

METHOD FOR AUTOMATICALLY TESTING AND CONTROLLING SURFACE-ACTIVE CONTENTS IN AQUEOUS SOLUTIONS USED IN A PROCESS

CROSS-REFERENCE TO RELATED APPLICATIONS

This application claims priority under 35 U.S.C. §371 to International Application No. PCT/EP99/01939, filed Mar. 23, 1999, which claims priority to German Patent No. DE 198 14 500.4, filed Apr. 1, 1998.

BACKGROUND OF THE INVENTION

1. Field of the Invention

This invention relates to a method for the automatic monitoring and control of aqueous process solutions containing nonionic, anionic and/or cationic surfactants. Examples of such process solutions are lyes for the large-scale washing of textiles, cleaning baths for hard surfaces and surfactant-containing iron phosphating solutions. The method is designed in particular for technical process solutions in the metalworking industry, such as in car manufacture. It makes it possible to monitor automatically the functional capacity, as characterised by the parameter "surfactant content", of the process solution and, if necessary, to supplement the process solution automatically or by external request, or to introduce other bath maintenance measures. The method is in particular so designed that the results of the surfactant determinations are transmitted to a location removed from the process solution. In addition, it is possible to intervene in the automatic measurement procedure from a location removed from the process solution or to initiate repeat metering or other bath maintenance measures. The "location removed from the process solution" may lie, for example, in a higher-level process control system, in a control room of the works in which the process solution is located, or else at a point outside the works.

2. Description of Related Art

The cleaning of metal parts prior to the processing thereof represents a conventional requirement in the metal-working industry. The metal parts may be contaminated, for example, with pigment soil, dust, metal abrasion, corrosion preventing oils, coolants or mould release agents. Prior to the processing, such as in particular prior to an anti-corrosion treatment (e.g. phosphating, chromating, anodising, reaction with complex fluorides etc.), or prior to a painting, such impurities must be removed by means of a suitable cleaner solution. Spraying, dipping or combined processes are considered for this. If surfactant-containing aqueous process solutions are used for the cleaning, which additionally contain phosphoric acid, a so-called non-film-forming phosphating is carried out simultaneously along with the cleaning. The cleaned metal parts are in so-doing coated simultaneously with a corrosion-proofing amorphous phosphate and/or oxide layer. Processes of this type are used widely in the metal-working industry as combined cleaning and corrosion-proofing processes. When applied to iron-containing materials, they are termed "iron phosphating".

Non-phosphating industrial cleaners in the metal-working industry are, as a rule, alkaline (pH values about 7 and above, for example from 9 to 12). The basic components are alkalis (alkali metal hydroxides, carbonates, silicates, phosphates, borates), as well as, for the present purposes nonionic, anionic and/or cationic surfactants. The cleaners frequently contain as additional auxiliary components complexing agents (gluconates, polyphosphates, salts of aminocarboxylic acids, such as ethylenediamine tetraacetate or nitrilotriacetate, salts of phosphonic acids, such as salts of hydroxyethane diphosphonic acid, phosphono-butane tricarboxylic acid, or other phosphonic or phosphonocarboxylic acids), anti-corrosive agents, such as salts of carboxylic acids having 6 to 12 carbon atoms, alkanolamines, and foam inhibitors, such as end group-capped alkoxylates of alcohols having 6 to 16 carbon atoms in the alkyl radical. If the cleaner baths do not contain any anionic surfactants, cationic surfactants may be used. The cleaners may in addition contain both nonionic and ionic surfactants.

The cleaners generally contain as nonionic surfactants ethoxylates, propoxylates and/or ethoxylates/propoxylates of alcohols or alkylamines having 6 to 16 carbon atoms in the alkyl radical, which may also be end group-capped. Alkyl sulfates, fatty alcohol ether sulfates and alkyl sulfonates are widely used as anionic surfactants. Alkylbenzene sulfonates are still encountered, but are disadvantageous in environmental terms. There are considered as cationic surfactants, in particular cationic alkyl ammonium compounds having at least one alkyl radical of 8 or more carbon atoms.

It is known in the prior art to determine manually the nonionic surfactants in aqueous process solutions, such as in cleaner baths, by means of a color indicator. The conventional procedure in this case is to add to a sample taken from the process solution a reagent which forms a color complex with nonionic surfactants. Such color complex is preferably extracted into an organic solvent not miscible in all proportions with water and the light absorption thereof then determined photometrically at a particular wavelength. Tetrabromophenolphthalein ethyl ester, for example, may be used as the reagent for forming the color complex. Prior to the extraction into an organic solvent, preferably into a chlorinated hydrocarbon, the process solution is in this case mixed with a buffer system having a pH of 7.

It is further known to determine nonionic surfactants in the presence of ionic surfactants. The ionic surfactants are here separated from the sample by ion exchangers. The nonionic surfactants not bound in the ion exchanger are determined from the refractive index of the process solution leaving the exchanger column.

Anionic and cationic surfactants in aqueous process solutions may be detected, for example, by titration with Hyamin® 1622 (=N-benzyl-N,N-dimethyl-N-4-(1,1,3,3,-tetramethylbutyl)phenoxyethoxyethylammonium chloride) and potentiometric end-point determination. For this, the sample is mixed with a known quantity of Na-dodecyl sulfate, titration with Hyamin is carried out and the end point of the titration is determined using an ion-sensitive electrode.

Alternatively, anionic surfactants may also be determined by titration with 1,3-didecyl-2-methylimidazolium chloride. An electrode having an ion-sensitive membrane is used as detector. The electrode potential depends on the concentration of the test ions in the process solution.

Depending on the outcome of this surfactant determination involving the deployment of personnel, the operating personnel of the plant supplement the process solution with one or more supplementary components. The procedure thus makes it necessary for operating personnel to be in attendance at the plant site at least during the periods of the surfactant determination. The procedure is personnel-intensive, therefore, in particular in multi-shift operation. The documenting of the results for quality control and quality assurance purposes entails additional expenditure.

SUMMARY

Conversely, an object of the present invention is to automate and document the monitoring of process solutions by surfactant determination in such a way that at least the results of the surfactant determination are stored on a data carrier and/or outputted. Preferably the measuring equipment used is itself to be checked and calibrated and an alarm message transmitted to a remote point in the event of a malfunction. Furthermore, it should preferably be possible to check the functional capacity of the measuring equipment and the measuring results from a remote point. It should also be possible to intervene in the measurement procedure and in the maintenance measures for the process solutions from a remote point. The number of personnel deployed on the monitoring and the control of the process solutions is to be reduced by the desired remote control.

DESCRIPTION OF THE PREFERRED EMBODIMENTS

This problem is solved by a method for the automatic monitoring and control of the content of surfactants of an aqueous process solution, wherein, under program control:

(a) a sample having a predetermined volume is taken from the aqueous process solution;

(b) if required, the sample is freed of solids;

(c) if required, the sample is diluted with water in a pre-set ratio or one determined as the result of a prior determination;

(d) the content of surfactants is determined by selective adsorption, electrochemically, chromatographically, by splitting into volatile compounds, stripping out of such volatile compounds and detection thereof, or by addition of a reagent which varies the interaction of the sample with electromagnetic radiation in proportion to the content of surfactants, and measurement of the variation of such interaction; and (e) the outcome of the determination is stored on a data carrier and/or used as a basis for further calculations and/or the outcome of the determination or of the further calculations is transmitted to a remote location.

For present purposes, an aqueous process solution is, in particular, a cleaning solution for hard surfaces, in particular for metal surfaces, or an iron phosphating solution. Process solutions of this type are known diversely in the prior art and are widely used in the metal-working industry.

The sample volume taken in (a) may be programmed permanently into the control section of the measuring equipment to be used for the method. Preferably, the size of the sample volume may be varied from a remote point. The control program may further be created in such a way that it makes the sample volume to be used dependent on the outcome of a previous measurement. For example, a correspondingly greater sample volume may be selected, the smaller is the surfactant content of the process solution. The accuracy of the surfactant determination may be optimized in this way.

When reference is made to a "remote location" in the context of the method according to the present invention, there is meant a location which is not located in direct or at least in visual contact with the process solution. The remote location may, for example, be a central process control system which, as part of an overall process for the surface treatment of the metal parts, monitors and controls a cleaner bath as a subsidiary function. The "remote location" may also be a central control room, from which the overall process is monitored and controlled and which is, for example, located in a different room to the process solution. There is also to be regarded as a "remote location", however, a point outside the works in which the process solution is located. It becomes possible in this way for the process solution to be monitored and controlled by specialists who are stationed outside the works in which the latter is located. In this way, it is necessary far less frequently for specialist personnel to be stationed at the location of the process solution.

Suitable data lines, with which the results of the surfactant determinations, as well as control commands, may be transmitted, are known.

Between the taking of the sample and the actual measurement, it may be desirable to free the sample of solids in the optional step (b). This is not necessary in the case of a process solution loaded only slightly with solids. If the solids content is excessively high, however, valves of the measurement equipment may become clogged and sensors become dirty. It is recommended, therefore, that solids be removed from the sample. This may take place automatically by filtration or alternatively by use of a cyclone or a centrifuge.

In (c), the sample is, if required, diluted with water in a pre-set ratio or one established as the result of a predetermination. In (d) the content of surfactants is determined by various methods which will be explained in detail below.

The outcome of the determination may then be stored on a data carrier in step (e). Additionally or alternatively thereto, it may be used as the basis for further calculations. In addition, the outcome of the determination or the outcome of the further calculations may be transmitted to a remote location and stored once again on a data carrier and/or outputted there. By "outputting of the outcome of the determination" is meant that the latter is either forwarded to a higher-level process control system or displayed on a screen so as to be discernible to a human or printed out. The location of the display or the outputting of the outcome may be the "remote location" indicated above. It is preferable that the results of the individual determinations are stored on a data carrier at least for a pre-set time interval, so that they may then be evaluated, for example for quality assurance purposes. The results of the surfactant determinations do not, however, have to be outputted directly as such or stored on data carriers. Instead they may also be utilized directly as a basis for further calculations, wherein the results of these further calculations are displayed or stored. For example, instead of the respective current surfactant content, the trend in the surfactant concentration and/or the relative change thereof may be displayed. Or the current surfactant contents are converted into "% of the target content".

In the simplest case, the method according to the present invention operates in such a way that (a) to (e) are repeated according to a pre-set time interval. The pre-set time interval is determined by the requirements of the operator of the process solution and may include any time interval from a few minutes to several days. For a quality control, it is preferable that the pre-set time intervals lie, for example, between 5 minutes and 2 hours. For example, a measurement may be carried out every 15 minutes.

The method according to the present invention may, however, also be carried out in such a way that (a) to (e) are repeated after time intervals which become progressively shorter the more the results of two successive determinations differ from one another. The control system for the method according to the present invention may therefore itself decide whether the time intervals between the individual determinations are to be shortened or lengthened. It is naturally necessary to pre-set in the control system the instruction as to what time intervals are to be selected for what differences between the results of successive determinations.

In addition, the method according to the present invention may be carried out in such a way that (a) to (e) are performed at any time on the basis of an external request. In this way, for example, an immediate monitoring of the surfactant content of the process solution may be undertaken if quality problems are detected in successive steps. The measurement of the surfactant content may therefore be time-controlled (according to fixed time intervals) or event-controlled (in the event of changes detected or by external requests).

Preferably, the method according to the present invention is carried out in such a way that the measuring equipment used is itself monitored and if necessary re-calibrated. It may be provided in this connection that, after a pre-set time interval or after a pre-set number of determinations or on the basis of an external request, the functional capacity of the measuring equipment used is checked by control measurements of one or more standard solutions. A standard process solution having known surfactant content is measured for the checking. This checking is closest to reality if there is used as the standard solution a standard process solution whose composition approximates as closely as possible to the process solution to be checked.

In the method according to the present invention it may also be provided that the functional capacity of the measuring equipment is checked by the check measurement of one or more standard solutions if the results of two successive measurements differ by a pre-set amount. In this way it may be distinguished whether differences discovered in the surfactant content of the process solution are real and require bath maintenance measures or whether they are caused by a fault in the measurement system.

Depending on the outcome of the checking of the measuring equipment used, the determinations of the surfactant content which have been conducted between the current and the preceding control measurements may be provided with a status code which indicates the reliability of said determinations. If, for example, successive control measurements for the checking of the measuring equipment used have shown that the latter is operating correctly, the determinations of the surfactant content may be provided with a status code "in order". If the results of the control measurements differ by a pre-set minimum amount, the determinations of the surfactant content which have been conducted in the meantime may, for example, be provided with the status code "doubtful".

In addition it may be provided that, depending on the outcome of the checking of the measuring equipment used, the automatic determination of the surfactant content is continued and/or one or more of the following steps is carried out: analysis of differences discovered, correction of the measuring equipment, termination of the determination of the surfactant content, sending of a status message or an alarm signal to a higher-level process control system or a monitoring unit, i.e. at a remote location. The measuring equipment may therefore, if required, itself decide according to pre-set criteria whether it has sufficient functional capacity that the determinations of the surfactant content may be continued, or whether differences are detected which make manual intervention necessary.

The method may further be so designed that the surfactants whose content in the process solution is to be determined are nonionic surfactants. The procedure to be adopted for the determination thereof may be such that a reagent is added in (d) which varies, in proportion to the content of nonionic surfactants, the interaction of the sample with electromagnetic radiation, and measures the variation of such interaction.

For example, the reagent may be a complex of two substances A and B, wherein the nonionic surfactants displace substance B from the complex with substance A and in so doing the color or fluorescence properties of substance B change. For example, substance B may be a fluorescent substance or a dye which is able to complex with, for example, dextrans or starch as an example of a substance A. As a component of the complex, substance B has particular color or fluorescence properties. If it is displaced from the complex, such properties change. By measuring the light absorption or the fluorescent radiation, it may be detected what portion of substance B is not complexed with A. Substance A is here selected in such a way that, on the addition of nonionic surfactants, substance B is displaced from the complex and a complex with the nonionic surfactants is formed instead. The quantity of substance B displaced from the complex with A is then proportional to the quantity of nonionic surfactants added. The quantity of nonionic surfactants added may be deduced from the change in the light absorption or the fluorescence, such change being caused by the amount of B liberated.

For example, there may be used as reagent a salt of a cationic dye with tetraphenylborate anions. Nonionic surfactants may displace the dye from the salt after they have been converted into a cationic complex with barium by the addition of barium ions. This method of converting nonionic surfactants into cationically charged complexes and thereby making them accessible to reactions which respond to cations is also described in the literature as the "activation" of nonionic surfactants. The method is described, for example, in Vytras K, Dvorakova V and Zeeman I (1989) Analyst 114, p. 1435 ff. The amount of the cationic dye liberated from the reagent is proportional to the amount of the nonionic surfactants present. If the absorption spectrum of the dye changes during the liberation, the amount of dye liberated may be determined by the photometric measurement of a suitable absorption band.

Such method of determination may be simplified if there is used as reagent a salt of a cationic dye which is soluble only in an organic solvent immiscible with water, while the liberated dye itself is water-soluble and leads to a coloration of the aqueous phase. The reverse procedure is naturally also possible: a water-soluble salt of an organic dye is used, wherein the liberated dye is soluble only in an organic phase. By liberation of the dye in exchange for the nonionic surfactants and extraction of the liberated dye into the respective other phase, it may be determined photometrically in the latter in a simple manner.

Such method of determination is also suitable for the determination of cationic surfactants. Since the latter are already positively charged, the "activation" with barium cations described above is superfluous.

In addition the reagent may be a substance which forms a complex with the anionic surfactants themselves, which has different color or fluorescence properties to the free reagent. For example, the reagent may be colorless in the visible region, while the complex thereof with nonionic surfactants absorbs electromagnetic radiation in the visible region, i.e has a color. Or the maximum of the light absorption, i.e. the color, of the uncombined reagent differs from that of the complex with the nonionic surfactants. The reagent may also, however, show particular fluorescence properties which vary during the complex formation with the nonionic surfactants. For example, the free reagent may fluoresce, while the complex formation with the nonionic surfactants quenches the fluorescence. In all cases it is possible, by measuring the light absorption to be pre-set or the fluorescent radiation, to determine the concentration of the complex of reagent and nonionic surfactants and hence the concentration of the nonionic surfactants themselves.

Preferably there is added in (d) a reagent which forms a complex with the nonionic surfactants which may be extracted into an organic solvent not miscible in all proportions with water. Thereafter, an extraction of the complex consisting of nonionic surfactants and added reagent into the organic solvent not miscible in all proportions with water is carried out. This may take place by intensive mixing of the two phases, for example by shaking or preferably by stirring. The mixing of the two phases is terminated after the extraction, so that a phase separation into an aqueous and an organic phase occurs. If required the completeness of the phase separation may be checked by suitable methods, such as determination of the electrical conductivity or measurement of the clouding by light absorption or light scatter.

This is followed by the actual measurement of the content of nonionic surfactants. For this, the organic phase, which contains the complex consisting of nonionic surfactants and added reagent, is exposed to an electromagnetic radiation which may interact with the complex dissolved in the organic phase. For example, there may be used as electromagnetic radiation visible or ultraviolet radiation whose absorption by the complex consisting of nonionic surfactants and added reagent is determined. It is also possible, however, for a reagent to be used whose complex with the nonionic surfactants produces a characteristic signal during nuclear resonance or electron spin resonance measurements. The signal strength, expressed as the weakening of an electromagnetic vibration in the corresponding frequency band (absorption), may be correlated with the concentration of the complex. Instead of absorption effects, emission effects may also be utilized to determine the concentration. For example, a reagent may be selected whose complex with nonionic surfactants in the organic solvent absorbs electromagnetic radiation of a particular wavelength and emits in turn electromagnetic radiation of a greater wavelength whose intensity is measured. An example of this is the measurement of the fluorescent radiation during the irradiation of the sample with visible or ultraviolet light.

The interaction of the organic phase with electromagnetic radiation may in principle take place directly after completion of the phase separation in the same vessel in which the phase separation is carried out. Depending on the method of measurement used to determine the interaction of the organic phase with electromagnetic radiation, it is, however, preferable to draw off the organic phase or a part thereof and to feed it to the actual measuring equipment along a line. It is in particular possible in this way to provide suitable cells for the measurement. Accordingly a preferred embodiment of the present invention involves, after (f), separating the organic phase from the aqueous phase and feeding it to the measuring equipment. Such separation of the organic phase is particularly recommended if the organic solvent not miscible in all proportions with water is a halogen-containing solvent with a density higher than water. After carrying out the phase separation, the organic phase is then located in the bottom part of the vessel and may be drawn off downwards.

As examples of halogen-containing solvents there are considered dichloromethane or higher-boiling halogenated hydrocarbons, in particular chlorinated or fluorinated hydrocarbons, such as trichlorotrifluoroethane. Such solvents must be disposed of after use in accordance with the local statutory provisions. As this may be expensive, there is the possibility of preparing the used solvent again, for example by treatment with activated carbon and/or by distillation, and re-using it for the measurement process.

In a preferred embodiment of the present invention, there is added as reagent an agent which undergoes a color reaction with the nonionic surfactant in the organic phase. The interaction of the organic phase with electromagnetic radiation may be measured as the light absorption at a pre-set wavelength. A conventional photometer is suitable for this purpose. For example, tetrabromophenolphthalein ethyl ester may be used as color reagent. In this case, the sample of the aqueous process solution must be mixed with a buffer system having a pH of about 7. Such a buffer system may, for example, be an aqueous process solution of dihydrogenphosphates and hydrogenphosphates. A procedure is adopted here such that the amount of the buffer solution is substantially greater than the sample amount of the surfactant-containing process solution.

If tetrabromophenolphthalein ethyl ester is used as color reagent, the measurement of the light absorption in (g) is preferably carried out at a wavelength of 610 nm.

In the preferred embodiment of the use of 3,3,5,5-tetrabromophenolphthalein ethyl ester as color reagent the determination of the content of nonionic surfactants may take place as follows:

an indicator solution is prepared which contains 100 mg of 3,3,5,5-tetrabromophenolphthalein ethyl ester in 100 ml of ethanol. In addition, a buffer solution is prepared by mixing 200 ml of a commercial buffer solution having a pH of 7 (potassium dihydrogenphosphate/disodium hydrogenphosphate) and 500 ml of a 3.0 M potassium chloride solution with 1000 ml of water.

For the carrying out of the determination, 18 ml of the buffer solution is placed in a suitable vessel. 50 $\mu$l of the sample solution is then added. The combined solutions are stirred for about 3 minutes and 20 ml of dichloro-methane is then added. The vessel contents are then mixed vigorously for about 1 minute. The phase separation is then awaited, which may require, for example, 20 minutes. Thereafter, the organic phase is removed and measured in a photometer at a wavelength of 610 nm. A 10 mm cell, for example, is suitable as the analysis cell. The surfactant content of the sample solution is determined by means of a calibration curve.

If the surfactant content is low to a degree such that the determination is unreliable, the volume of the sample used for the measurement may be increased. If the surfactant content is high to a degree such that a light absorption of more than 0.9 occurs, it is recommended that the sample be diluted prior to the measurement.

Irrespective of the method selected, a correlation between the strength of the test signal and the concentration of the surfactants must be obtained, by a prior calibration with surfactant solutions of known concentration, and stored. If the light absorption is measured, the calibration may also take place by means of suitable colored glasses. As an alternative to a prior calibration, conclusions may be drawn on the surfactant content of the sample by the addition of surfactant/reagent complex in known concentration or by multiple topping up and renewed measurement of the interaction with electromagnetic radiation.

As an alternative to a determination of the interaction with electromagnetic radiation of a reagent combined with the nonionic surfactant or displaced from a complex by the latter, the content of nonionic surfactants may be determined chromatographically. For this any oils and fats present are preferably removed from the sample at the outset. This may be carried out, for example, using an absorbent. Thereafter, the sample, which optionally contains ionic surfactants, is passed to an anion and/or cation exchange column, which preferably resembles in its layout a column for high-pressure liquid chromatography. The concentration of the nonionic surfactants in the solution freed of the ionic surfactants, which solution leaves the exchange column, is preferably determined by means of the refractive index. The quantitative evaluation is preferably conducted here by the method of the external standard. The measurement takes place by a comparison with pure solvent from the comparison cell and solvent containing material for analysis from the test cell of the detector. Water or a water-methanol mixture are considered as solvents.

Prior to commencement of a measurement series, a HPLC-type ion exchange system must be calibrated and the comparison cell of the detector rinsed with the solvent for 20 minutes. Solutions having varying concentrations of the non-ionic surfactants to be determined are used for the calibration. Calibration and sample solutions must be degassed in an ultrasonic bath, for example, for 5 minutes prior to injection into the HPLC-type system. Such degassing is important on account of the sensitivity of the refractive index detection to different solvent qualities.

If the sample solution is mixed with methanol prior to the application to the HPLC-type ion exchange column, insoluble salts may precipitate out. The latter must be filtered off through a microfilter prior to the feeding of the sample into the HPLC-type system.

This method is known for the off-line determination of unsulfonated portions in organic sulfates or sulfonates (DIN EN 8799).

In addition, the following procedure is suitable for the determination of the nonionic surfactants: the nonionic surfactants are cleaved using hydrogen halide, preferably using hydrogen iodide, with the formation of volatile alkyl halides, preferably of alkyl iodides. The volatile alkyl halides are stripped out by the injection of a gas current into the sample and are detected in a suitable detector. For example, an "Electron Capture Detector" is suitable for this purpose. This method is known as a laboratory method for characterising fatty alcohol ethoxylates (DGF Einheitsmethode H-III 17 (1994)).

The surfactants may also be anionic surfactants. The content thereof in the sample solution is preferably determined electrochemically in (d). For this, the anionic surfactants are titrated with suitable reagents, the titration being monitored by the variation of the electric potential of a suitable test electrode.

For example, a procedure may be adopted here such that the pH of the sample is set to between 3 and 4, preferably to about 3.5, the sample is titrated with a titration reagent in the presence of an ion-sensitive membrane electrode and the variation in the electrode potential is measured. The sensitivity of this method can be increased by the sample being mixed with an alcohol having 1 to 3 carbon atoms, preferably with methanol. As titration reagent, 1,3-didecyl-2-methylimidazolium chloride is preferred. An ion-sensitive membrane electrode, preferably having a PVC membrane serves as test electrode. Such an electrode is known as a "high sense electrode". A silver electrode is preferably used as reference electrode. The potential formation takes place by an as specific interaction as possible between the ion carrier contained in the PVC membrane and the ions that are to be determined in the test solution. Such interaction leads in an equilibrium reaction to a transference of the test ions out of the test solution into the membrane and hence to the formation of an electric potential difference at the test solution/membrane phase boundary. Such potential difference may be measured potentiometrically (without current) against a reference electrode. The degree of the ion transfer out of the test solution into the membrane is concentration-dependent. The relationship between the test ion concentration and the electric potential may be described theoretically by the Nernst equation. Because of possible disturbance, it is preferable, however, to establish the relationship between electrode potential and test ion concentration by calibration using comparison solutions.

In addition to anionic surfactants, cationic surfactants may also be determined in the process solution to be monitored. A method may be used for this which is also suitable for determining anionic surfactants. In this method also the determination takes place electrochemically: a predetermined quantity of Na-dodecyl sulfate is added to the sample, the sample is titrated with Hyamin (N-benzyl-N,N-dimethyl-N-4-(1,1,3,3-tetramethylbutyl) phenoxyethoxyethyl ammonium chloride) and the titration end product is determined using an electrode sensitive to ionic surfactants.

In addition to the methods mentioned above, methods are suitable for determining surfactants in which the surfactants are absorbed on suitable surfaces and effects which are attributable to the covering of the surfaces with the surfactants are measured. Since the covering of the surfaces with the surfactants may be assumed to be proportional to the surfactant content below the saturation limit, it is possible after suitable calibration to draw conclusions as to the surfactant content of the sample solution from the changes in properties of the surfactant-covered surfaces.

For example, the surfactants may be absorbed at the surface of an oscillator crystal and the variation in the oscillation frequency of the oscillator crystal measured. A further method involves absorbing the surfactants at the, optionally suitably pre-treated, surface of a light guide. This leads to a variation in the refractive index on the passage of light out of the light guide into the surrounding medium, which variation becomes noticeable in the conductivity of the light guide for light. Depending on the refractive index, the light in the light guide is attenuated in varying degrees or, in the event of loss of total reflection at the light guide end, no longer appears at all. The degree of covering of the light guide surface with surfactants, and hence the surfactant content in the surrounding medium, may be determined by comparing the light intensity exiting at the end of the light guide with that fed in at the beginning. The collapse of the total reflection occurs at a particular threshold value of the surfactant content, which may likewise be utilized to characterise the surfactant content of the process solution.

The method according to the present invention is applicable to any process solutions. It is particularly designed for process solutions in the metal-working industry, for example in car manufacture. For example, the aqueous process solution may be a cleaner solution. Such cleaner solutions are used, for example, for the cleaning of car bodies prior to phosphatizing. For the monitoring and the control of such a cleaner solution, it may be provided that, on falling short of a pre-set minimum value for the content of surfactants or in response to an external request, a device is activated which meters one or more supplementary components into the cleaner solution. A supplementary component is considered, for example, to be a supplementary solution which contains all of the active substances of the cleaner solution in the correct quantitative ratio. The supplementary solution may therefore contain, in addition to the checked surfactants, further active substances of the cleaner solution, such as further surfactants, builder substances, alkalis, complexing agents and corrosion inhibitors. Alternatively to this, the supplementary solution may contain only the surfactants, while the other active agents of the cleaner solution are repeat-metered at a clock pulse or under throughput control, if necessary according to separate specifications.

In this connection, the size of the added portion itself or, in the case of exactly pre-set added portions, the time intervals between the individual additions may be varied. This may take place, for example, by means of metering pumps or else be weight-controlled. In the method according to the present invention, it is therefore provided, on the one hand, that, in the event of particular deviations from the target value (in particular if the functional capacity of the measuring equipment has been determined by the check measurements), a particular quantity of supplementary component is repeat-metered into the process solution. On the other hand, such subsequent metering may also, however, be undertaken in response to an external request, for example from a remote location, irrespective of the current content of surfactants.

In a further embodiment of the present invention, the process solution is supplemented as a function of throughput with a pre-set amount of supplementary component per unit put through. For example, it may be determined for a cleaning bath for car bodies what amount of supplementary component is added per cleaned body. The monitoring according to the present invention of the surfactant content or of the interruption of the basic metering then serves to monitor and to document the success of such pre-set addition, and also to achieve by additional result-dependent fine metering a more constant mode of operation of the cleaning bath. In this way, quality fluctuations are reduced.

Preferably the measurement system used in the method according to the present invention is designed so that it checks automatically the filling levels and/or the consumption of the reagents used (color or fluorescence reagent, titrating solution, standard and test solutions, solvents, buffer solution or ancillary solutions) and issues a warning message if a pre-set minimum filling level is not met. The measuring equipment may thereby be prevented from becoming incapable of functioning because it lacks the required chemicals. The checking of the filling levels may take place by known methods. For example, the vessels containing the chemicals may stand on a balance which records the respective weight of the chemicals. Or a float is introduced. Alternatively a minimum filling level may be checked by a conductivity electrode which is immersed in the vessel containing the chemical. The warning message to be emitted by the measuring equipment is preferably transmitted to the remote location, so that the relevant measures may be initiated from there. In general, it is preferably provided in the method according to the present invention that the results of the determinations and/or of the check measurements and/or of the calibrations and/or the status signals are transmitted continuously or at pre-set time intervals and/or on request to a remote location. In this way checking personnel who do not have to be present at the location of the process solution are informed regularly of the current surfactant content thereof. Depending on the outcome of the determinations and the check measurements, corrective measures required may be undertaken either automatically via a process control system or by manual intervention.

The method according to the present invention naturally pre-supposes that the corresponding equipment is available. The latter comprises a controller, preferably a computerized controller, which controls the measuring sequence on a time- or event-dependent basis. It must in addition comprise the requisite reagent vessels, tubes, valves, metering and measuring devices etc. for controlling and measuring the sample flows. The items of equipment must be suited to the intended use, for example be made of stainless steel and/or of plastics material. The control electronics of the measuring equipment should comprise a corresponding input-output interface, in order to able to communicate with a remote location.

The method according to the present invention makes it possible on the one hand to check the surfactant content of process solutions on site and to initiate pre-set corrective measures without manual intervention. Process safety is enhanced in this way and a constantly reliable process result achieved. Departures from the target values may be detected promptly and corrected automatically or manually before the process result is affected. On the other hand, the test data are preferably transmitted to a remote location, so that operating or supervisory personnel are also informed regularly of the state of the process solution if they are not located in the immediate vicinity thereof. The staffing costs for the monitoring and control of the process solution may be reduced considerably in this way. The requirements of a modern quality assurance system are met by the documenting of the data collected in the method according to the present invention. The chemical consumption may be documented and optimized.

What is claimed is:

1. A method for the automatic monitoring and control of the content of surfactants of an aqueous process solution, the method comprising the following steps, performed under program control:
   (a) taking a sample having a predetermined volume from the aqueous process solution;
   (b) determining the content of surfactants in the sample utilizing measuring equipment capable of analyzing the sample by selective adsorption, electrochemically, chromatographically, by splitting into volatile compounds, stripping out of such volatile compounds and detection thereof, or by addition of a reagent which varies the interaction of the sample with electromagnetic radiation in proportion to the content of surfactants, and measurement of the variation of such interaction;
   (c) outputting the result of step (b);
   (d) repeating steps (a)–(c); and
   (e) determining the surfactant content of one or more standard solutions if the results of step (b) on two consecutive drawn samples differs by a preselected value to check the functional capacity of the measuring equipment.

2. The method of claim 1 further comprising the step of removing solids from the sample prior to the step of determining the content of surfactants.

3. The method of claim 1 further comprising the step of diluting the sample with water in a pre-set ratio prior to the step of determining the content of surfactants.

4. The method of claim 1 further comprising the step of diluting the sample with water in a ratio determined as the result of a prior determination prior to the step of determining the content of surfactants.

5. The method of claim 1 wherein the aqueous process solution is selected from the group consisting of cleaning solutions and iron phosphating solutions.

6. The method of claim 1 wherein the step of outputting comprises storing the result of step (b) on a data carrier.

7. The method of claim 6 further comprising the step of transmitting the result of the determination to a remote location.

8. The method of claim 1 further comprising the step of using the result of step (b) as a basis for obtaining a result of further calculations.

9. The method of claim 8 further comprising the step of transmitting the result of further calculations to a remote location.

10. The method of claim 1 wherein steps (a) through (c) are automatically repeated after a specified time interval.

11. The method of claim 10 further comprising the step of adjusting the duration of the specified time interval based on a comparison of the results of step (b) on consecutive drawn samples.

12. The method of claim 1 further comprising the step of inputting an external request to initiate steps (a) through (c).

13. The method of claim 1 further comprising one or more steps selected from the group consisting of:

analyzing the results of a plurality of surfactant content determinations, automatically terminating the process, and activating a detectable signal.

14. The method of claim 1 wherein the corrective action comprises one or more steps selected from the group consisting of automatically determining the level of one or more reagents, and adding a pre-set amount of one or more reagents when a pre-set minimum filling level is not met.

15. The method of claim 14 further comprising the step of activating a detectable signal in response to a determination of a preselected level of one or more reagents.

16. The method of claim 1 further comprising the step of automatically adding one or more surfactants to the aqueous process solution in response to the result of step (b) being a preselected value.

17. The method of claim 1 wherein the aqueous process solution contains one or more surfactants selected from the group consisting of nonionic surfactants, cationic surfactants, and anionic surfactants.

18. The method of claim 17 wherein the step of determining comprises adding a reagent which varies the interaction of the sample with electromagnetic radiation, and measuring the variation of such interaction.

19. The method of claim 17 wherein the step of determining comprises adding a reagent which forms a complex with the nonionic surfactants, the complex being extractable into an organic solvent that is not miscible in all proportions with water, extracting the complex into an organic solvent that is not miscible in all proportions with water, and measuring the content of nonionic surfactants by exposing the organic solvent containing the complex to electromagnetic radiation.

20. The method of claim 19 further comprising the step of adding as reagent an agent which undergoes a color reaction with the nonionic surfactant.

21. The method of claim 17 wherein the step of determining comprises titrating a surfactant selected from the group consisting of cationic surfactants and anionic surfactants and monitoring the titration by the variation of the electric potential of a suitable test electrode.

22. The method of claim 1 wherein the step of determining comprises determining the content of nonionic surfactants chromatographically.

23. The method of claim 1 wherein the step of determining comprises absorbing the surfactants on a suitable surface and measuring effects which are attributable to the covering of the surface with the surfactants.

24. The method of claim 23 wherein the surface is selected from the group consisting of a surface of an oscillator crystal and a surface of a light guide.

* * * * *

UNITED STATES PATENT AND TRADEMARK OFFICE
CERTIFICATE OF CORRECTION

PATENT NO.     : 6,617,165 B1
DATED          : September 9, 2003
INVENTOR(S)    : Opitz et al.

It is certified that error appears in the above-identified patent and that said Letters Patent is hereby corrected as shown below:

Title page,
Item [73], Assignee, delete "Dusseldorf", and insert therefore -- Duesseldorf --.

Column 12,
Line 49, delete "and".
Line 54, delete ".", and insert therefore -- ; and conducting a corrective action for controlling the content of surfactants. --.

Signed and Sealed this

Nineteenth Day of October, 2004

JON W. DUDAS
*Director of the United States Patent and Trademark Office*